United States Patent [19]

Walele et al.

[11] Patent Number: 5,271,930
[45] Date of Patent: Dec. 21, 1993

[54] BENZOATE ESTERS OF POLYALKOXYLATED BLOCK COPOLYMERS

[75] Inventors: Ismail I. Walele, Saddle Brook, N.J.; Nicholas J. Scarangella, West Nyack, N.Y.; Anthony Ansaldi, Stanhope; Ann M. Andrews, Saddle Brook; Samad A. Syed, Jersey City, all of N.J.

[73] Assignee: Finetex, Inc., Elmwood Park, N.J.

[21] Appl. No.: 795,916

[22] Filed: Nov. 20, 1991

[51] Int. Cl.$^5$ .................. A61K 31/765; A61K 7/075; A61K 7/32

[52] U.S. Cl. .................. 424/78.08; 424/60; 424/70; 424/71; 424/401; 424/75

[58] Field of Search .................. 424/78.08, 60, 70, 71, 424/75, 401; 560/112; 514/668

[56] References Cited

U.S. PATENT DOCUMENTS

| | | | |
|---|---|---|---|
| 3,022,335 | 2/1962 | Lundsted | 528/419 |
| 3,101,374 | 12/1963 | Patton, Jr. et al. | 544/398 |
| 3,639,575 | 2/1972 | Schmolka | 424/78.08 |
| 4,323,693 | 4/1982 | Scala, Jr. | 560/103 |
| 4,359,478 | 11/1982 | Schmolka | 514/533 |
| 4,791,097 | 12/1988 | Walele et al. | 560/112 |

FOREIGN PATENT DOCUMENTS 815991 7/1959 United Kingdom ................ 560/112

*Primary Examiner*—Thurman H. Page
*Assistant Examiner*—Peter F. Kulkosky
*Attorney, Agent, or Firm*—Weingram & Zall

[57] ABSTRACT

Benzoic acid esters of a polyalkoxylated block copolymer, i.e. PLURONICS, exhibit enhanced characteristics that make these esters ideally suited for skin and hair care compositions. These esters demonstrate enhanced capabilities as foam boosters, emollients, conditioners, clarifiers, solubilizers, and carriers (dilutents). In addition, both oxybenzone and benzocaine can be solubilized by these esters.

16 Claims, No Drawings

BENZOATE ESTERS OF POLYALKOXYLATED BLOCK COPOLYMERS

BACKGROUND OF THE INVENTION

1. Field of the Invention

This invention relates generally to improved ester compositions, and more particularly to certain benzoic acid esters of polyalkoxylated block copolymers which are useful as foam modifiers, emollients, conditioners, and clarifiers.

2. Description of the Prior Art

Numerous references describe the production and use of benzoic acid esters. None of these references teach or suggest the specific novel benzoate esters of this invention or the use of these benzoate esters as foam modifiers, emollients, clarity enhancers, or conditioners for shampoo and/or conditioners. More specifically:

U.S. Pat. No. 3,916,008 to Green. et al, describes the use of a class of esters which are useful for the control of serum cholesterol levels in animals and man. One group of esters included within the invention include esters of the surfactant sold under the trade name "Tetronic 701" and "Tetronic 702". Reference is made to formula II wherein the groups $R_1$, $R_2$, $R_3$, and $R_4$ include benzyl and substituted benzyl. Preferred esters are tetraesters (Col 2, line 18) and tetra-benzoate esters (col 2., line 61–Col. 3, line 5) (see example 1, Col. 3).

U.S. Pat. No. 3,932,659 to Green, et al., describes tetronic non-ionic surfactants as useful in reducing serum cholesterol levels in animals and man.

U.S. Pat. No. 4,243,799 to Mueller, et al., describes polybutylene glycol carboxylic acid diesters and their method of production. The compound may be a diester of a carboxyl containing aromatic radical.

U.S. Pat. Nos. 4,275,222, and 4,322,545 to Scala, Jr. describes benzoic acid esters of linear primary alcohols and their use as diluents, solvents, plasticizers, and liquid carriers.

U.S. Pat. No. 4,322,545 to Scala, Jr. describes benzoic acid esters of isostearyl ($C_{18}$) alcohol and their use in toiletry and cosmetic formulations.

U.S. Pat. No. 4,323,693 to Scala, Jr. describes linear and branched alcohols and their use in toiletry and cosmetic formulations.

U.S. Pat. No. 4,323,694 to Scala, Jr. describes benzoic acid esters of alcohols.

U.S. Pat. No. 4,359,478 to Schmolka describes certain polyoxybutylene-polyoxyethylene block copolymers and their mono or diesters for use in a diet as a hypocholesterolaemic agent. The diesters are of the formula:

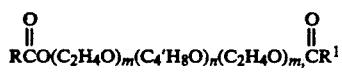

wherein R are $R_1$ and H or aryl or aliphatic with suitable esters being benzoate esters.

U.S. Pat. No. 4,431,837 to Geria describes long chain aliphatic hydrocarbon ethoxylated alcohol benzoates having a small degree of ethoxylation and believed to be of the general formula:

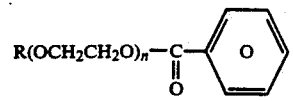

in which R is a long chain aliphatic hydrocarbon radical having from about 8 to about 18 carbon atoms and n is a number no greater than about 5. These benzoates are useful as vehicles in pharmaceutical, cosmetic and toiletry preparations.

U.S. Pat. No. 4,791,097 to Walele, et al. describes benzoate esters used as foam enhancers. The benzoate ester is of the formula:

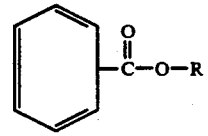

wherein R is

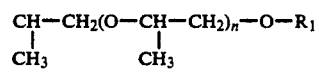

wherein n is 9–16 and $R_1$ is branched linear alkyl of 3 to 22 carbon atoms, or of the formula:

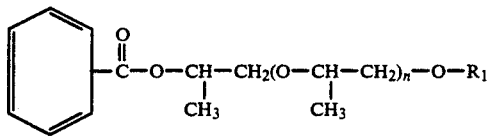

wherein n is 9 to 16 and $R_1$ is a branched or linear alkyl of 3 to 22 atoms.

Further, polyalkoxylated block copolymers sold by BASF under the trademark PLURONIC are well known surfactants.

SUMMARY OF THE INVENTION

An object of this invention is to provide improved benzoic acid ester compositions.

A further object of this invention is to provide novel benzoic acid esters which may serve as foam boosters, emollients, conditioners, clarifiers, solubilizers, and carriers or diluents.

Another object of this invention is to provide esters that enhance the clarity and foam boosting characteristics of hair care products such as shampoos and conditioners.

Still another object of this invention is to provide esters that enhance the wet comb, dry comb, and fly-away characteristics of hair care products.

A further object of this invention is to provide esters with enhanced abilities to solubilize oxybenzone and benzocaine.

A still further object of this invention is to provide esters with an improved affinity for water/propylene glycol/glycerin.

Another object of this invention is to provide esters that are highly soluble in mineral oil.

A still further object of this invention is to provide esters which will enhance the look and feel characteristics of skin and hair care products such as soaps, tanning lotions, antiperspirants, and hand, face or body lotions with vitamins.

This invention is directed to benzoic acid esters of polyethoxylated block copolymers (commercially available under the tradename PLURONIC) and polypropoxylated block copolymers (commercially available under the tradename PLURONIC R). PLURONIC and PLURONIC R copolymers are available from BASF Corp. Chemicals division.

This invention is further directed to a benzoic acid ester of a polyethoxylated block copolymer propoxylated isostearyl alcohol.

Another compound of this invention is a benzoic acid ester of a poly propoxylated block copolymer of ethoxylated isostearyl alcohol.

DETAILED DESCRIPTION OF THE INVENTION

The benzoic acid esters of this invention are produced by reacting benzoic acid with the PLURONIC surfactants, polyalkoxylated block polymers. Preferably, stannous oxalate is used as a catalyst. It is contemplated, however, that any method of producing such benzoic acid esters can be utilized as long as such method does not interfere with the intended use of the ester. In particular, the process for producing the esters should permit them to be purified to a substantially pure condition. By the use of the term "substantially pure", it is meant that the compositions do not contain impurities which would interfere with the intended use of the ester.

Block copolymers of propylene oxide and ethylene oxide are commercially available as PLURONIC and PLURONIC R surfactants from BASF Corporation's Chemical Division.

A PLURONIC surfactant is a polyethoxylated block copolymer of propoxylated propylene glycol and is formed by the controlled addition of propylene oxide to the two hydroxyl groups of propylene glycol. The addition of ethylene oxide sandwiches this hydrophobe between hydrophilic groups. The structure of these PLURONIC surfactants is:

$$HO-(CH_2CH_2O)_x-(CH_2CHO)_y-(CH_2CH_2O)_x-H$$
$$\phantom{HO-(CH_2CH_2O)_x-(}CH_3$$

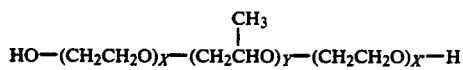

Such a structure has a preferred molecular weight of from 1000 to 3300 and has from 10% to 50% ethylene oxide (by weight).

A PLURONIC R surfactant is also available. The PLURONIC R surfactant is a polypropoxylated block copolymer of ethoxylated ethylene glycol prepared by adding ethylene oxide to ethylene glycol to provide a hydrophile of the desired molecular weight. Hydrophobic blocks are attached to the outside of the molecule by adding propylene oxide. The structure of the PLURONIC R surfactants is:

$$HO-(CHCH_2O)_x-(CH_2CH_2O)_y-(CH_2CHO)_x-H$$
$$\phantom{HO-(}CH_3\phantom{CH_2O)_x-(CH_2CH_2O)_y-(CH_2C}CH_3$$

Such a structure has a preferred molecular weight of from 1000 to 3300 and has from 10% to 20% ethylene oxide (by weight).

The benzoate esters of the present invention are produced by reacting the PLURONIC and PLURONIC R copolymers with benzoic acid to produce novel esters of this invention and the esters used in this invention.

The structure of these benzoate esters is:

Polyethoxylated Block Copolymer of Propoxylated Propylene Glycol:

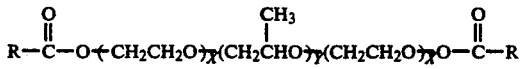

Polypropoxylated Block Copolymer of Ethoxylated Propylene Glycol.

wherein

wherein x and y are number of moles of PO and EO ranging from 2 to 100, preferably 2 through 30.

Optionally, the esters of this invention may be half esters, i.e. one of the R substituent is H.

Preferred PLURONICS or PLURONICS R have an average molecular weight of from 1000 to 3300.

This invention is further directed to a benzoic acid ester of a polyethoxylated block copolymer of propoxylated propylene glycol wherein the composition is of the formula:

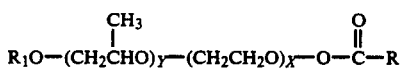

wherein
R is

;

$R_1$ is isostearyl substituent: and
wherein x and y are each 1 through 30.

Another compound of this invention is a benzoic acid ester of a polypropoxylated block copolymer of ethoxylated isostearyl alcohol wherein the composition is of the formula:

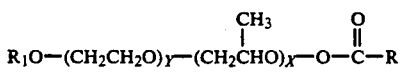

wherein

R is

;

$R_1$ is an isostearyl substituent; and
wherein x and y are each 1 through 30.

The compositions of this invention are useful as:
Emollients,—solubilizers
Moisturizers,—plasticizers
Sunscreen vehicles/solvents
Hair conditioners/detanglers
Wetting agents for powders, ($TiO_2$; ZnO ...)
De-oilers/degreasers
Emulsifiers/Co-Emulsifiers
Viscosity-modifiers
Foam-modifiers
Facial cleansers The foregoing list is only exemplary of the type of composition in which the benzoic acid esters of this invention may be used and, as such, is not to be considered limiting.

The amount of ester used in an aqueous surfactant composition is dependent in the type of composition desired, the type and quantity of other ingredients used, e.g. cosmetic ingredients, and the amount and type of functional additives that are utilized. Typically, the amount ranges from about 0.5% to about 50% by weight of the aqueous surfactant composition. Preferably, from about 0.5% to about 5.0% of benzoic acid esters of this invention are use.

The aforedescribed benzoic acid esters have unique properties. In particular, they have foam modifying properties. By "foam modification" herein it is meant that the benzoic acid esters confer any or all of the following properties upon a surfactant composition:
Flash foam increase
Foam volume increase
Foam viscosity increase or decrease
Foam cell size increase or decrease While the particular foam modification is dependent upon the benzoic acid ester and surfactant of choice, no surfactant investigated has been observed to suffer a suppression of foam volume due to the presence of any of the benzoic acid esters investigated herein, i.e. none of the benzoic acid esters investigated were defoamers. Additionally, they have other properties which make them suitable for use as emollient carriers and for use as solvents.

The compounds of this invention possess other unusual physicochemical properties, in particular, they have high spreading coefficients, which can make them beneficial and unique components of sophisticated delivery systems—such as in hand, face, and body creams and lotions.

The benzoate esters of this invention may be used in skin care compositions. The amount used in skin care compositions is dependent on the type of skin care compositions, the type and quantity of cosmetic ingredients used and the amount and type of functional additives. Typically the amount ranges from about 0.5% to about 80%, by weight, of the skin care compositions. For example, a facial cream may only have about 0.5%, whereas a massage oil may have up to about 80%, by weight. Still higher amounts may be used in, for example bath oils, e.g. 95%.

Further, the benzoate esters described herein are solvents and/or vehicles for ultraviolet (UV) absorbers. Such esters may also function as plasticizers for polymers contained in skin care compositions, may be auxiliary suspending agents capable of assisting in the suspension of ingredients in skin care compositions and also may function as a dye leveling agent and dye carrier. Thus, the benzoate ester when used in skin care compositions serves not only as an emollient and carrier but also exhibits one or more other functions.

The aforedescribed benzoic acid esters have the following properties:
1. Water solubility/dispersibility.
2. Ease of emulsification.
3. Emulsifier/co-emulsifier with other emollients.
4. Emolliency at body temperature with good afterfeel.
5. Lack of greasiness, pleasant skin feel.
6. Lack of oiliness while imparting good lubrication.
7. Viscosity improvements without extraneous thickeners.
8. Foam improvements with viscosity increases.
9. Low cloud points and pour points.
10. Unusually high spreading coefficient.
11. Bland odor.
12. Gel formation—ability to form gels with suspending agents.
13. Alcohol (ethanol) solubility.
14. Dispersibility in propylene glycol/glycerine/water.
15. Solubility in mineral oil.
16. Allows more water in some systems.
17. Low toxicity.
18. Acid, alkaline stability.
19. Solvents for many common skin and hair care ingredients.
20. Pearlescence in emulsions without pearlescing agents additives, including, sunscreens and over-the-counter therapy 'actives'.

The following are non-limiting examples of the compositions of this invention and the uses of these compositions in hair and skin care compositions wherein foam modification, clarity, emulsification, or conditioning properties are needed.

EXAMPLE 1

Preparation of PPG-3-Isosteareth-9-Benzoate

A mixture of 218 gms. of AROSURF 66-PE-12 (PPG-3-Isosteareth-9 from Sherex Chem. Co.) and 62 mgms. of sodium borohydride was treated under nitrogen purge at 50° C. for ½ hour. Then 32 gms. of benzoic acid and 0.40 gms. of stannous oxalate was added. This mixture was heated to 175° C. over a half hour period and then heated to 245°–250° C. This reaction mixture was held at 245°–250° C. for 2 hours. During the last hour of the reaction, a vacuum of 20–25" Hg was applied. The acid value at the end of the reaction was 6.90 mgm. KOH/gm.

Upon cooling to 90° C., 2.0 gm. hydrogen peroxide was added to bleach the slight darkening in the reaction mixture. The reaction mixture was then cooled to 30° C. Upon treatment for 10 minutes with 1.0 gm. CELATOM FW-60, the crude yield of 237 gms. was filtered at 50°–60° C. A clear yellow liquid was obtained.

Then 150 gms. of this ester was treated with 3.4 gms of sodium carbonate, 3.4 gm. of sodium sulfate and 102.2 gm. of water at 80°–85° C. The wet top layer of the mixture (162.5 gms.) was then treated with two washes; each consisting of 3.5 gm of sodium sulfate and 100 gms. of water. The product layer upon separation was 160 gms. which was dried at 90°–100° C. and under vacuum of 27" Hg.

Upon cooling to 60°–65° C. and the addition of 0.25 gms. of CELATOM FW-60, the ester was filtered using Whatman #2 paper. A clear refined liquid ester was obtained with a yield of 132 gms.

EXAMPLE 2

Preparation of PLURONIC 25-R-2 Benzoate

A mixture of 791 gms. of PLURONIC 25-R-2, 124.5 gms. of benzoic acid and 1.8 gms. of stannous oxalate was heated, under nitrogen purge, to 105° C. over a one hour period. The reaction mixture was then further heated to 245°–247° C. over the next one hour period and held thereat for 3 hours. At the end of this reaction period, the acid value was 1.14 mgms. KOH/gm.

The distillate was continuously removed and collected. The mixture was cooled to 110° C. at which point 9 gms. of hydrogen peroxide was added. A yield of 827 gms. of the ester was obtained.

CELATOM FW-60 at 0.4% was then added and the product filtered at 70° C. using Whatman #42 paper. The yield produced was 750 gms. of refined ester.

EXAMPLE 3

Preparation of PLURONIC 31-R-1 Benzoate

Under nitrogen purge, a mixture of 613 gms. of PLURONIC 31-R-1 and 170 mgms. of sodium borohydride was kept at 50° C. with stirring for ½ hour. Then 46.2 gm. of benzoic acid and 1.70 gms. of stannous oxalate was added. The reaction mixture was brought to 215° C. over a ¾ hour period and then further raised to 230° C. over the next 2 hours. During this reaction period, distillate was continuously collected. The reaction was further carried out at 230° C. for 2 hours during which the mass darkened in color.

The acid value at the end of the reaction was 0.6 mgms. KOH/gm. The yield was 630 gms. of ester. The mass was cooled to 100°–110° C. and then 3 gms. of hydrogen peroxide was added. Upon standing overnight and then treating with CELATOM FW-60 and MAGNESOL at 0.2% each, the resulting mixture was filtered using Whatman #4 paper on a laboratory filter press. A crystal clear nearly water white liquid was obtained. The yield produced was 600 gms. of the refined ester.

EXAMPLE 4

Preparation of PLURONIC 31-R-1 Benzoate

A mixture of 232.5 gms. of PLURONIC 31-R-1 and 62.5 mgms. of sodium borahydride was stirred at 50° C. under nitrogen purge for ½ hour. Then 17.50 gms. of benzoic acid and 0.375 gms. of stannous oxalate was added. The reaction mixture was then heated to 200°–215° C. over a ½ hour period. This reaction mixture was further heated to 235°–240° C. and held thereat for 3 hours. A vacuum of 10–15" Hg was applied to remove any residual water of reaction. The acid value of the reaction mixture was 20.77 mgm. KOH/gm. The reaction yielded 240 gms. net of crude ester in the reaction flask when cooled.

EXAMPLE 4A

The crude ester prepared in Example 4 was further refined by treating 25 gms. of this crude ester with 0.5 gm. of sodium hydroxide (50% solution), 0.5 gms. of sodium sulfate and 25 gms. of water. An additional 0.25 gms. of sodium hydroxide (50% solution), was also used. Two layers resulted: The top oily layer of the ester which was retained and the bottom layer which was drained off. The wet ester was then treated with 40 gms. of water and 0.9 gm. of sodium sulfate. The two layers instantly separated. The ester was further treated with 80 gms. water and 1 gm. sodium sulfate. At 25° C., the bottom layer was the product. This procedure yielded 25.45 gms. of the wet ester.

EXAMPLE 4B

The crude ester prepared in Example 4 was further refined by treating 130 gms. of the crude ester with 3.5 gms. of sodium hydroxide (50% solution), 3 gms. of sodium sulfate and 130 gms. of water. The mixture was heated to 80°–85° C. at which time two distinct phases formed. The bottom aqueous layer was drained off.

The wet ester was then treated with 5 gms. of sodium sulfate and 200 gms. of water at 80° C. The top layer of the product was separated from the bottom aqueous layer. This wet ester was further treated with 5 gms. of sodium sulfate and 200 gms. of water at 80°–85° C. The product, the top layer, was then dried at 110°–120° C. with a vacuum of 15–20" Hg. After cooling and the addition of CELATOM FW-60 (from Eagle Pitcher Industries), the ester was filtered. A yield of 110 gms. of the refined dry ester was obtained.

EXAMPLE 5

Preparation of PLURONIC L-35 Benzoate

Under nitrogen purge, 264 gms. of PLURONIC L-35 and 60 mgms. of sodium borohydride were mixed at 40° C. for ½ hour. Then 36 gms. of benzoic acid and 0.6 gms of stannous oxalate was added. The reaction mass was then heated to 215° C. over a 1¾ hour period. The temperature was then raised to 225° C. and held thereat for 4 hours. The acid value at the end of the reaction was 1.54 mgms. KOH/gm. The yield was 292 gms. of crude ester upon cooling to 70° C.

The crude ester was further treated by washing 272 gms. of the crude ester with 200 gms. of water, 1 gm. of sodium carbonate and 15 gms. of sodium sulfate at 50° C. The top layer of the resulting wet product, when separated, weighed 320 gms. This wet yield was further washed with 200 gms. of water containing 15 gms. of sodium sulfate and 0.5 gms. of acetic acid at 40° C. Upon standing the two layers separated.

The top layer of the product yielded 312 gms. of wet ester. Dehydration was carried out at 110° C. and 15–25" Hg vacuum. The product, when cooled to 60° C., was treated with 0.25% of CELATOM FW-60 and MAGNESOL and filtered. A crystal clear liquid and a yield of 215 gms. of refined ester was obtained.

EXAMPLE 6

Preparation of PLURONIC L-35 Benzoate

A mixture of 282 gms. of PLURONIC L-35, 18 gms. of benzoic acid and 0.9 gms. of stannous oxalate was heated to 70° C. under nitrogen purge. The temperature was further raised to 220° C. over 2½ hours while continuously collecting the distillate. The acid value was 12–67 mgms KOH/gm. The reaction was then held at 220° C. for 1 hour. At this point, the acid value was 3.85 mgm. KOH/gm. The yield was 281 gms. of the ester.

The ester was then treated at 80° C. with 135 gms. of water containing 18 gms. of sodium sulfate and 3 gms. of sodium carbonate. The wet ester layer (260 gms.) was separated from the bottom layer of wash-water and further treated with 150 gms. of water containing 1 gm. of acetic acid and 20 gms. of sodium sulfate at 60° C. Upon separation of the top layer as product, the yield was 265 gms of wet ester. This wet ester was dehydrated at 110° C. and 15–25" Hg vacuum. Upon cooling and treating with CELATOM FW-60 and MAGNESOL, 0.2% each, and with 0.1% PRECOFLAC PB-33 (cellulose) at 50°–55° C., the ester was filtered giving a clear viscous liquid and a net yield of 208 gms. of refined ester.

EXAMPLE 7

Preparation of PLURONIC L-35 Benzoate

A mixture of 869 gms. of PLURONIC L-35, 118.5 gms. of benzoic acid and 2.0 gms. of stannous oxalate was heated to 220° C. over 1½ reaction mixture was held at 220°–230° C. for 4 hours at which time the acid value was found to be 1.53 mgm. KOH/gm. After cooling to 25° C., the net yield was 942 gms. of crude ester.

The crude ester was then treated at 80°–85° C. with 700 gms. of water containing 2 gms. of sodium carbonate, 52 gms. of sodium sulfate and 2.4 gms. of the hydrogen peroxide. The product (1072 gms.) was separated. The top layer was further treated with 770 gms. of water, 50 gm of sodium sulfate and 1.5 gm. of glacial acetic acid. The product after separation was dehydrated at 105°–110° C. and 20–27" Hg vacuum. Upon cooling to 60°–70° C., the product was filtered using CELATOM FW-60 and MAGNESOL at a rate of 0.2% each. The yield was 879 gms. of the refined ester.

EXAMPLE 8

Preparation of PLURONIC L-62 Benzoate

A mixture of 1812.74 gms. of PLURONIC L-62, 201.42 gms. of benzoic acid and 6.04 gms. of stannous oxalate was brought to a temperature of 240° C. under nitrogen purge. The reaction was continued at 240° C. for about 4 hours. At this point, the acid value was 1.4 mgms KOH/gm.

The mixture was cooled to 86° C. and 5 gms. of hydrogen peroxide was added with mixing. The crude ester was subjected to washing at 75° C. with 1817 gms. of water containing 19.0 gms. of sodium carbonate, 87.0 gms. of sodium sulfate and 10 gms. of hydrogen peroxide. The product layer was separated from the wash water. The yield was 2247 gms. of wet ester This wet ester was subjected to a second wash with 705.5 gms. of water and 122.6 gms of sodium sulfate. Wash water with a pH of about 10.00 was separated and the wet ester layer (2294 gms) was then subjected to a third wash with 1752 gms. of water containing 125 gm. of sodium sulfate. To this wash-water was added 3 gms. of glacial acetic acid to achieve a pH of 5.5–6.0. The mixture was brought to 75° C. for separation of the two layers. After separation, this wet ester was dehydrated at 110° C. under nitrogen purge and vacuum. Upon drying, the ester was filtered using CELATOM FW-60 and MAGNESOL. The yield was 1751 gms. of the refined ester.

EXAMPLE 9

Preparation of PLURONIC L-64 Benzoate

For ½ hour, 213.5. gms. of PLURONIC L-64 and 58 mgms. of sodium borohydride were mixed while being heated to 75° C. Under nitrogen purge, 19.3 gms. of benzoic acid and 0.35 gm. of stannous oxalate were added at 60° C. and 70° C. respectively. The reaction mixture was then heated to 230° C. and reacted thereat for 4½ hours. The acid value at the end of the reaction period was 2.34 mgms. KOH/gm. Upon cooling, the yield was 225 gms. of crude ester.

This ester was treated with 200 gm. of water containing 2.5 gms. of sodium carbonate, 8 gms. of sodium sulfate, 2 gms. of hydrogen peroxide at 80°–85° C. and then at 100°–105° C. A very viscous, semi-emulsified top layer of wet ester was collected. This top layer weighed 245 gms.

This wet ester was then further treated with 150 gms. of water, 23 gm of sodium sulfate and 2.5 gms. of acetic acid at 80°–85° C. The wet semi-emulsified top layer was collected. This top layer weighed 270 gms.

Upon drying at 105°–115° C. under nitrogen purge and a vacuum of up to 20" Hg, a very clear liquid was obtained. The yield of 192 gms. of ester was treated with 0.2% CELATOM FW-60 and 0.1% PRECOFLOC PB-33 (pure cellulose) and filtered. A crystal clear liquid ester was obtained.

EXAMPLE 10

Preparation of PLURONIC L-64 Benzoate

For 1 hour, 978 gms. of PLURONIC L-64 and 300 gms. of sodium borohydride were mixed at 62°–64° C. gms. under nitrogen purge. Then 88.4 gms. of benzoic acid and 1.6 gms. of stannous oxalate were added. The mixture was then heated to 212° C. a 1 hour period.

While reacting, the mixture temperature was further raised to 230° C. over the next 1½ hours while continuously distilling off the water of reaction. The reaction mixture was then held at 230° C. for 2 hours. At this point the acid value was 5–7 mgms. KOH/gm. When cooled to 25° C., the yield was 981 gms. of crude ester.

This crude ester was subjected to washing at 80°–85° C. with 865 gms. of water containing 7.8 gms. of sodium carbonate and 21.6 gms. of sodium sulfate An additional 34 gms. of sodium sulfate predissolved in 80 gms. of water was added to facilitate separation. The wash liquid was at a pH of 8.0 and the product layer showed an acidity of 0.6 mgms. KOH/GMS.

The product layer collected was 1100 gms. This product was further treated with 970 gms. of water, 88 gms. of sodium sulfate and 1.6 gms. of acetic acid. This mixture separated into layers at 82° C.

The product layer was separated and subjected to dehydration at 110° C. and a vacuum of 20–27" Hg. Upon dehydration, cooling and treatment with 0.2% of CELATOM FW-60 and 0.2% MAGNESOL at 60°–70° C., the product was filtered. The yield was 884 gms. of the refined ester.

EXAMPLE 11

Description of Reactants With Benzoic Acid

| Reactants With Benzoic Acid | Ex No. | Average Molecular Weight | % ETHYLENE OXIDE | BLOCKS AVERAGE NO. OF MOLES | | |
|---|---|---|---|---|---|---|
| PLURONIC SERIES | | | | (EO) | (PO) | (EO) |
| L-31 | | 1100 | 10 | 2 | 16 | 2 |
| L-35 | 5–7 | 1900 | 50 | 11 | 16 | 11 |
| L-62 | 8 | 2500 | 20 | 8 | 30 | 8 |
| L-64 | 9,10 | 2900 | 40 | 13 | 30 | 13 |
| PLURONIC R SERIES | | | | (PO) | (EO) | (PO) |
| 17-R-1 | | 1900 | 10 | 12 | 4 | 12 |
| 17-R-2 | | 2150 | 20 | 12 | 9 | 12 |
| 25-R-1 | | 2700 | 10 | 18 | 6 | 18 |
| 25-R-2 | 2 | 3100 | 20 | 18 | 14 | 18 |
| 31-R-1 | 3,4 | 3250 | 10 | 21 | 7 | 21 |

EO is ethylene oxide.
PO is propylene oxide.

EXAMPLE 12

Effect of Esters on Clarity and Foam of Clear Conditioning Shampoo

A shampoo base which is clear, mild and conditioning is prepared by charging the water and heating it to 60°–70° C. Then the following ingredients are added in the order given, while maintaining the temperature of the shampoo base until all ingredients are fully incorporated. Preservative, fragrance and color can be added, as desired. The viscosity of the shampoo base increases upon cooling.

| Component | % by Weight |
|---|---|
| Standapol A (Ammonium Lauryl Sulfate)[1] | 15.0 |
| TAURANOL I-78-6 (Sodium Cocoyl Isethionate) | 10.0 |
| FINQUAT CT (Quaternium 75) | 5.0 |
| AMINOL HCA (Cocamide DEA) | 5.0 |
| Water | 65.0 |

Esters were added at a 3% level directly into the shampoo base to determine the effect on clarity and foam versus the control without the ester. The following data illustrates that the new esters not only maintain clarity but also enhance the foam performance. The old esters have traditionally been foam depressants and, in addition, have formed emulsions when placed with water systems.

| Ester | Appearance | | Foam Height* | |
|---|---|---|---|---|
| | Initial | Overnight | 0 min. | 5 min. |
| Control without Ester | Clear | Clear | 293** | 293** |
| PRIOR ART ESTERS | | | | |
| TN[1] | Emulsion | Sep. | 220 | 210 |
| IPM[2] | Emulsion | Sep. | 245 | 245 |
| P.G. dicaprylate/ dicaprate | Emulsion | Sep. | 200 | 200 |
| Caprylic/ Capric T.G. | Emulsion | Sep. | 273** | 273** |
| NEW ESTERS BASED ON PLURONIC BENZOATE | | | | |
| PL-62 | Clear | Clear | 315** | 315** |
| PL-35 | Clear | Clear | 340** | 340** |
| PL-35 | Clear | Clear | 320 | 320 |
| PL-64 | Clear | Clear | 330 | 330** |

*0.5% Soln.
**Avg. of 2 trials
[1]$C_{12-15}$ alkyl benzoate
[2]isopropylpalmitate

EXAMPLE 13

Conditioning Effect on Hair

The method used comprised rinsing each one gram tress sample under warm water. Placing one of each tress into a formulation. Letting each sit in solution for five minutes. Rinsing under warm water. Hanging and performing wet comb, dry comb and flyaway.

The shampoo base formula comprised:

| Phase | Chemicals | % |
|---|---|---|
| A | Ammonium Lauryl Sulfate | 30.0 |
| | Cocoamide diethanolamine | 5.0 |
| | Water | 41.25 |
| B | Ammonium Chloride | 2.0 |
| | Water | 6.0 |
| C | Water | 15.75 (Q.S.) |

This shampoo base was formulated as follows:
1. Combine phase A chemicals.
2. Heat To 55° C.
3. Combine phase B chemicals
4. When phase A chemicals are at 55° C., add phase B chemicals to phase A chemicals
5. Mix for 5 minutes
6. Cool and continue mixing until chemicals reach room temperature Note that the 15.75% water (phase C) left out of the formula will be Q.S. with each conditioner at 5.0% level and water.

Each batch consists of:

| | |
|---|---|
| 84.25% | base |
| 10.75% | distilled water |
| 5.00% | ester or dimethiocone |
| 100.00 | |

The results were as follows:

| Batch | Wet Comb | Dry Comb | Fly Away |
|---|---|---|---|
| Shampoo base (base) | 9 | 5 | 3 inches |
| Base with *dimethicone | 5 | 1 | 2 inches |
| Base with *dimethicone copolyol | 7 | 2.5 | 6 inches |
| Base with PL-35 benzoate ester | 7 | 1.5 | 2.5 inches |
| Base with PL-64 Benzoate Ester | 6 | 2 | 4.0 inches |
| Base with PL-62 benzoate ester | 8 | 2 | 2 inches |
| Base with PL-35 benzoate (½) ester | 5 | 3 | 3 inches |

*Dimethicone 200 fluid - Dow Corning Corp.
*Dimethicone copolyol - Dow Corning Corp.

The rating scale used was: 1=best, 10=worst. The above results show that dimethicone and PL-35 benzoate (½) ester are both comparable in their effect on wet hair.

The dry comb results shown that the dimethicone and PL-35 benzoate ester affect dry comb. Although, the PL-35 benzoate ester is not as improved on wet comb as is the PL-35 benzoate (½) ester.

Both the dimethicone and PL-62 benzoate ester help to control flyaway.

Overall, the dimethicone is the best emollient in this study. The results obtained for both the PL-62 benzoate ester and PL-35 benzoate ester also indicate that these esters are primary emollients.

EXAMPLE 14

Solubility of Actives Compounds in Esters of the Invention

The solubility of both the commercially available esters and the esters of the invention were used in these tests are as follows:

bilize oxybenzone. In addition, an exceptional improvement was observed in solubilizing benzocaine.

For sunscreen applications, a known benefit of the prior art FINESOLV TN ester is its ability to solubilize oxybenzone. As the results show, the PL-35, PL-35 (½) and PL-64 esters can solubilize more oxybenzone than the TN ester.

The structure of the active ingredients used in these trials is as follows:

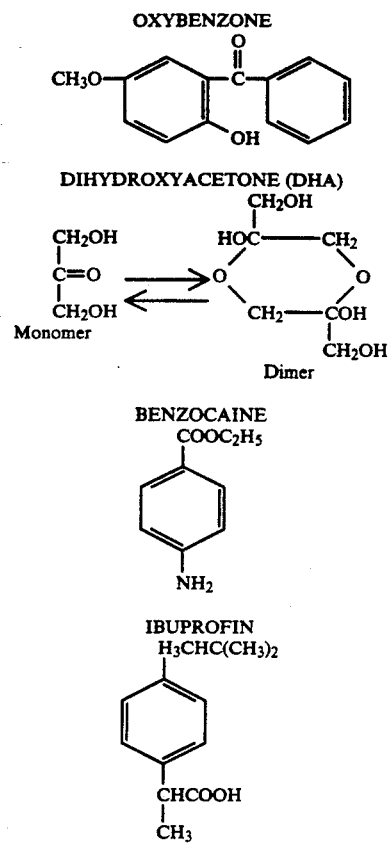

EXAMPLE 15

| Esters | Name | % SOLUBLE | | | |
|---|---|---|---|---|---|
| | | OXYBENZONE | DHA | BENZOCAINE | IBUPROFIN |
| COMMERCIAL ESTERS FINESOLV | | | | | |
| TN | C12-15 alkyl benzoate | 22 | <1 | 4.0 | 12.0 |
| SB | Isostearyl benzoate | 17 | <1 | 3.0 | 9 |
| BOD | Octyl dodecyl benzoate | 16 | <1 | 1.0 | 7.0 |
| P | PPG-15 stearoxyl benzoate | 21 | <1 | 11.0 | 20.0 |
| ESTERS OF INVENTION | | | | | |
| PL-62 | PLURONIC L-62 benzoate | 21 | <1 | 26.0 | N/A |
| PL-35 | PLURONIC L-35 benzoate | 25 | <1 | 30.0 | N/A |
| PL-35(½) | PLURONIC L-35 (½ ester benzoate) | 23 | <1 | 29.0 | N/A |
| PL-64 | PLURONIC L-64 benzoate | 23 | <1 | 29.0 | N/A |

*Average values rounded to nearest whole number
N/A = not applicable

The above results show that the esters of this invention have advantages over prior art esters. The esters of this invention demonstrated an enhanced ability to solu- Solubility/1 Gm of Ester/9 Gm of Solvent The solubility of both the commercially available and the experimental esters used in these trials are as follows:

|  | MINERAL | VOLATILE | PROP. |  |  |
|---|---|---|---|---|---|
| Ethanol | OIL | SILICONE | GLY | GLY. | H₂O |
| COMMERCIAL ESTERS |  |  |  |  |  |
| FINSOLV |  |  |  |  |  |
| TN[1] S | S |  | S | I | I | I |
| P[2] S | S |  | S | D | D | I |
| BOD[3] D | S |  | S | I | D | I |
| SB[4] S | S |  | S | I | I | I |
| EH-25[5] S | S |  | S | D | I | I |
| EXPERIMENTAL ESTERS |  |  |  |  |  |
| PL-62 S | S |  | I | D | D | Emul. |
| PL-35 S | I |  | I | D | D | Emul. |
| PL-35 (½) S | S |  | I | S | D | Emul. |
| PL-64 S | I |  | I | D | D | Emul. |

Where S = soluble,
I = insoluble
D = ] dispersible
[Emul = emulsion formed
[1]C₁₂₋₁₅ Alkyl-Benzoate
[2]Stearyl-Polypropoxy-Benzoate
[3]Octyl-Dodecyl-Benzoate
[4]Isostearyl-Benzoate
[5]C₁₂₋₁₅ Alkyl-Octanoate These results demonstrate that the solubility advantages of the experimental esters are in their improved affinity for water/propylene and glycol/glycerin. These esters produce clean systems at low concentrations of 3 to 5% with the aid of surfactants like Surfine AZI-A (carboxymethylate of ethoxylated nonyl phenol or Fizul MD-318C (oleamido-mida-sulfosucinate sodium).

In addition, both the PL-62 and PL-35(½) esters show unique properties in their solubility in mineral oil.

EXAMPLE 16

Effect of Esters on Clarity and Foam of Clear Conditioning Shampoo

The following prior art and esters of this invention were added at 3% level directly into a clear conditioning shampoo to determine the effect on clarity and foam versus the control shampoo without the ester. The results of these trials are as follows:

|  | Appearance |  | Foam Height* |  |
|---|---|---|---|---|
| Ester | Initial | Overnight | 0 min. | 5 min. |
| Control shampoo without ester | Clear | Clear | 293** | 293** |
| COMMERCIAL ESTERS FINESOLV |  |  |  |  |
| TN[1] | Emulsion | Sep. | 220 | 210 |
| IPM[2] | Emulsion | Sep. | 245 | 245 |
| P.G. dicaprylate/dicaprate | Emulsion | Sep. | 200 | 200 |
| Caprylic/Capric T.G. | Emulsion | Sep. | 273** | 273** |
| ESTERS OF THE INVENTION |  |  |  |  |
| PL-62 | Clear | Clear | 315* | 315* |
| PL-35 | Clear | Clear | 340** | 340** |
| PL-35 (½) | Clear | Clear | 320 | 320 |
| PL-64 | Clear | Clear | 330 | 330 |

*0.5% Soln.
**Avg. of 2 trials
[1]C₁₂-C₁₅ Alkyl-Benzoate
[2]Isopropyl-Palmitate

As these results indicate, all of the experimental esters can be added to shampoo systems without loss of clarity and with significant foam boosting capability. This is unique since esters typically reduce foam.

EXAMPLE 17

Skin Care Compositions of This Invention

A series of compositions can be prepared, such as:
(1) a liquid soap (Table 1)
(2) a self-tanning lotion (Table 2)
(3) an antiperspirant stick (Table 3)
(4) a water in oil lotion with vitamins (Table 4)

TABLE 1

| LIQUID SOAP (81-828C) | |
|---|---|
| COMPONENT | % by Weight |
| Distilled Water | 55.8 |
| Sodium C14-16 Olefin Sulfonate | 20.0 |
| Sodium Cocoyl Methyl Taurate | 10.0 |
| Lauramide DEA | 4.0 |
| Quaternium-75 | 2.0 |
| Glycol Stearate | 2.0 |
| Glycerin | 2.0 |
| PL-62-BENZOATE of Invention | 2.0 |
| DMDM Hydantoin | 0.2 |
| Sodium Chloride | 2.0 |

TABLE 2

| Self-Tanning Lotion (81-122D) | |
|---|---|
| COMPONENT | % by Weight |
| PEG-40 Stearate | 8.0 |
| Cetyl Alcohol | 1.0 |
| PL-62-BENZOATE of Invention | 6.0 |
| Tocopheryl Acetate | 3.0 |
| Distilled Water | 73.3 |
| Glycerine | 3.2 |
| Dihydroxyacetone | 5.0 |
| Diazolidinyl Urea, Propylene Glycol, Methylparaben, Propylparaben | 0.5 |

TABLE 3

| ANTIPERSPIRANT STICK | | |
|---|---|---|
|  | % BY WEIGHT | |
| Component | 81-20B | 81-20C |
| Cyclomethicone | 43.5 | 43.4 |
| Stearyl Alcohol | 23.0 | 23.0 |
| PL-35-BENZOATE of Invention | 5.0 | — |
| PL-62-BENZOATE of Invention | — | 5.0 |
| Hydrogenated Castol Oil | 2.0 | 2.0 |
| Steareth-20 | 1.0 | 1.0 |
| Silica | 0.5 | 0.5 |
| Aluminum Chlorhydrate | 25.0 | 25.0 |

TABLE 4

| WATER-IN-OIL LOTION WITH VITAMINS | | | |
|---|---|---|---|
|  | % by Weight | | |
| Component | 81-130A | 81-130B | 81-130D |
| Cyclo-methicone/Dimethicone Copolyol | 9.5 | 9.5 | 9.5 |
| Cyclo-methicone | 6.0 | 6.0 | 6.0 |
| Tocopheryl Acetate | 2.0 | 2.0 | 2.0 |
| Pareth 25-3 | 0.5 | 0.5 | 0.5 |
| PL-35-BENZOATE of Invention | 5.0 | — | — |
| PL-62-BENZOATE of Invention | — | 5.0 | — |
| PL-64-BENZOATE of Invention | — | — | 5.0 |
| Propylparaben | 0.15 | 0.15 | 0.15 |
| Distilled water | 72.7 | 72.7 | 72.7 |
| Sodium Chloride | 2.0 | 2.0 | 2.0 |

TABLE 4-continued

| WATER-IN-OIL LOTION WITH VITAMINS | | | |
|---|---|---|---|
| | % by Weight | | |
| Component | 81-130A | 81-130B | 81-130D |
| Methyl Paraben | 0.15 | 0.15 | 0.15 |
| Panthenol | 2.0 | 2.0 | 2.0 |

What is claimed is:

1. A dibenzoic acid ester of a polyethoxylated block polymer of propoxylated propylene glycol wherein the composition is of the formula:

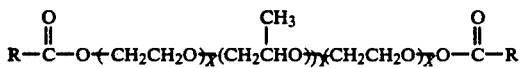

wherein
R is

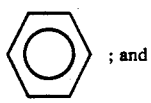
; and wherein x and y are each 2 to 100 and the block copolymer has a molecular weight of at 1000.

2. A dibenzoic acid ester of a polypropoxylated block copolymer of ethoxylated ethylene glycol wherein the composition is of the formula:

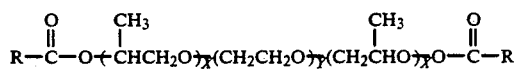

wherein
R is

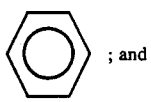
; and wherein x and y are each 2 to 100 and the block copolymer has a molecular weight of at least 100.

3. A monobenzoic acid ester of a polyethoxylated block copolymer of propoxylated propylene glycol wherein the composition is of the formula:

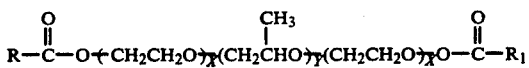

wherein
R=

;

$R_1$ is hydrogen; and
wherein x and y are each 2 to 100 and the block copolymer has a molecular weight of at least 1000.

4. A monobenzoic acid ester of a polypropoxylated block copolymer of ethoxylated ethylene glycol wherein the composition is of the formula:

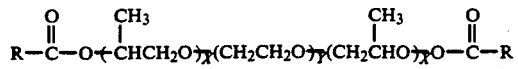

wherein
R=

;

$R_1$ is hydrogen; and
wherein x and y are each 2 to 100 and the block copolymer has a molecular weight of at least 1000.

5. The benzoic acid ester of claims 1, 2, 3, or 4 wherein x and y are each 2 to 30.

6. A conditioning shampoo containing the benzoic acid ester of claim 1 or 2.

7. A hair conditioner containing the benzoic acid ester of claim 1 or 2.

8. A sunscreening composition containing the benzoic acid ester of claim 1 or 2.

9. An emulsion comprising water and the benzoic acid ester of claim 1 or 2.

10. A liquid or solid soap containing the benzoic acid ester of claim 1 or 2.

11. A self-tanning composition containing the benzoic acid ester of claim 1 or 2.

12. An antiperspirant composition containing the benzoic acid ester of claim 1 or 2.

13. A skin care lotion with vitamin composition containing the benzoic acid ester of claim 1 or 2.

14. A benzoic acid ester of a polyethoxylated block copolymer of propoxylated propylene glycol wherein the composition is of the formula:

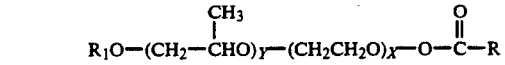

wherein
R is

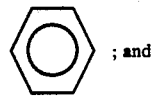
; and $R_1$ is an isostearyl substituent; and
wherein x and y are each 1 to 30 and the block copolymer has a molecular weight of a least 1000.

15. A benzoic acid ester of a polypropoxylated block copolymer of ethoxylated isostearyl alcohol wherein the composition is of the formula:

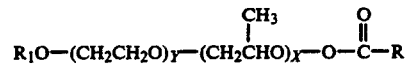

wherein
R is

;

$R_1$ is an isostearyl substituent; and
wherein x and y are each 1 through 30 and the block copolymer has a molecular weight of at least 1000.

16. The benzoic acid di-esters as in claim 1 or 2 having a molecular weight of 1,000–3,000.

* * * * *